United States Patent
Bartel et al.

(10) Patent No.: US 11,613,502 B2
(45) Date of Patent: Mar. 28, 2023

(54) CORE-SHELL CERAMIC PARTICLE COLLOIDAL GEL AND SOLID OXIDE FUEL CELL ELECTROLYTE

(71) Applicant: The Regents of the University of Colorado, Denver, CO (US)

(72) Inventors: Christopher Bartel, Boulder, CO (US); Alan W. Weimer, Niwot, CO (US); Rebecca Jean O'Toole, Boulder, CO (US); Maila Kodas, Carlisle, MA (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 16/347,585

(22) PCT Filed: Nov. 4, 2017

(86) PCT No.: PCT/US2017/060066
§ 371 (c)(1),
(2) Date: May 5, 2019

(87) PCT Pub. No.: WO2018/156218
PCT Pub. Date: Aug. 30, 2018

(65) Prior Publication Data
US 2019/0345068 A1    Nov. 14, 2019

Related U.S. Application Data

(60) Provisional application No. 62/520,655, filed on Jun. 16, 2017, provisional application No. 62/418,666, filed on Nov. 7, 2016.

(51) Int. Cl.
*H01M 8/1253* (2016.01)
*C04B 35/486* (2006.01)
(Continued)

(52) U.S. Cl.
CPC ........ *C04B 35/4885* (2013.01); *C04B 35/624* (2013.01); *C04B 35/62813* (2013.01);
(Continued)

(58) Field of Classification Search
None
See application file for complete search history.

(56) References Cited

U.S. PATENT DOCUMENTS 5,035,962 A * 7/1991 Jensen ................ H01M 4/9066
204/291
5,098,740 A    3/1992 Tewari
(Continued)

FOREIGN PATENT DOCUMENTS

CN    1246443 A     3/2000
CN    101054299 A   10/2007
(Continued)

OTHER PUBLICATIONS

5. Geuzens, G. Vanhoyland, J. D'Haen, S. Mullens, J. Luyten, M.K. Van Bael, H. Van den Rul, J. Mullens, Synthesis of zirconia-alumina and alumina-zirconia core-shell particles via a heterocoagulation mechanism, Journal of the European Ceramic Society, vol. 26, Issue 15, 2006, pp. 3133-3138. (Year: 2006).*
(Continued)

*Primary Examiner* — Lucas J. O'Donnell
(74) *Attorney, Agent, or Firm* — Snell & Wilmer L.L.P.

(57) ABSTRACT

Disclosed herein is a ceramic particle comprising a core substrate chosen from yttria-stabilized zirconia, partially stabilized zirconia, zirconium oxide, aluminum nitride, silicon nitride, silicon carbide, and cerium oxide, and a conformal coating of a sintering aid film having a thickness of less than three nanometers and covering the core substrate, and methods for producing the ceramic particle.

25 Claims, 6 Drawing Sheets

(51) Int. Cl.
    *C04B 35/488* (2006.01)
    *C04B 35/624* (2006.01)
    *C04B 35/628* (2006.01)
    *H01M 8/12* (2016.01)

(52) U.S. Cl.
    CPC ... *H01M 8/1253* (2013.01); *C04B 2235/3217* (2013.01); *C04B 2235/3246* (2013.01); *C04B 2235/6026* (2013.01); *H01M 2008/1293* (2013.01); *H01M 2300/0077* (2013.01)

(56) References Cited

U.S. PATENT DOCUMENTS

| | | | |
|---|---|---|---|
| 5,210,455 A | 5/1993 | Takeuchi et al. | |
| 5,273,942 A | 12/1993 | McCauley et al. | |
| 6,476,539 B1 * | 11/2002 | Takeuchi | H01L 41/43 310/330 |
| 6,613,383 B1 * | 9/2003 | George | B01J 2/006 427/212 |
| 7,396,862 B2 | 7/2008 | Weimer et al. | |
| 7,402,330 B2 | 7/2008 | Pfeifer et al. | |
| 7,799,419 B2 | 9/2010 | Brule et al. | |
| 7,811,918 B1 | 10/2010 | Dutta | |
| 8,691,717 B2 | 4/2014 | Lopez et al. | |
| 9,186,726 B2 | 11/2015 | Keane et al. | |
| 10,544,500 B2 | 1/2020 | Sun et al. | |
| 10,563,297 B2 | 2/2020 | Sun et al. | |
| 2003/0198417 A1 * | 10/2003 | Yamamoto | F16C 33/32 384/492 |
| 2005/0003192 A1 | 1/2005 | Atarashi et al. | |
| 2007/0142206 A1 * | 6/2007 | Binder | C04B 35/4885 501/103 |
| 2007/0280895 A1 | 12/2007 | Weimer et al. | |
| 2010/0055340 A1 * | 3/2010 | Park | B01J 2/04 427/452 |
| 2010/0297474 A1 | 11/2010 | Dameron | |
| 2011/0034319 A1 | 2/2011 | Villalobos et al. | |
| 2011/0198216 A1 * | 8/2011 | Larsen | H01M 8/1213 204/242 |
| 2012/0132953 A1 | 5/2012 | Becker et al. | |
| 2012/0301720 A1 | 11/2012 | Koban et al. | |
| 2016/0214165 A1 * | 7/2016 | Hoel | C04B 35/16 |
| 2016/0285122 A1 * | 9/2016 | El Batawi | H01M 4/8828 |
| 2017/0155169 A1 * | 6/2017 | Hitz | H01M 10/0585 |
| 2017/0275769 A1 * | 9/2017 | Lim | C01B 32/40 |
| 2018/0002235 A1 * | 1/2018 | Ito | C04B 35/486 |

FOREIGN PATENT DOCUMENTS

| | | |
|---|---|---|
| CN | 101075665 A | 11/2007 |
| CN | 101423398 A | 5/2009 |
| CN | 101746760 A | 6/2010 |
| CN | 101003907 B | 8/2010 |
| CN | 101164889 B | 9/2010 |
| CN | 102683722 A | 9/2012 |
| CN | 103242042 B | 5/2014 |
| CN | 104086176 A | 10/2014 |
| CN | 104355290 A | 2/2015 |
| CN | 106011791 A | 10/2016 |
| CN | 107540379 B | 8/2020 |
| JP | 2012069418 A | 4/2012 |
| JP | 6500523 B2 | 4/2019 |
| WO | 03008186 A1 | 1/2003 |

OTHER PUBLICATIONS

Travitzky et al, Additive Manufacturing of Ceramic-Based Materials, Advanced Engineering Materials 2014, 16, No. 6 (Year: 2014).*
ISR dated Jul. 12, 2018 for PCT/US17/60066, 2 pgs.
Written Opinion dated Dec. 2018 for PCT/US17/60066, 4 pgs.
Machine translation of description of Japanese Patent JP 6500523 B2.
Machine translation of description of Japanese Patent Application JP 2012069418 A.
Office Action in Japanese Application 2019523863, dated Aug. 2, 2021.
Machine translation of Office Action in Japanese Application 2019523863, dated Aug. 2, 2021.
Xu et al., "Effects of Al2O3 Content on the Sinterability and Mechanical Properties of Y-TZP Ceramics," Silicate Bulletin, No. 4, p. 40-42 (1997).
Ji et al., "Study on Influence of Doping of Al2O3 on Performance of Solid Oxide Electrolyte Material YSZ," Functional Materials, No. S1, pp. 53-54 and 61 (2001).
Hakim et al., "Conformal Nanocoating of zirconia nanoparticle by atomic layer deposition in a fluidized bed reactor," Nanotechnology 16 pp. 5375-5381 (2005).
Radford et al., "Zirconia electrolyte cells," Journal of Materials Science 14 pp. 59-65 (1979).
Translation of First Office Action and Search Report from Chinese Application No. CN201780075924, dated May 17, 2021.
Machine translation of description of Chinese Patent CN101003907B.
Machine translation of description of Chinese Patent CN101075665A.
Machine translation of description of Chinese Patent CN1246443A.
Machine translation of description of Chinese Patent CN104086176A.
Machine translation of description of Chinese Patent CN103242042B.
Machine translation of description of Chinese Patent CN101054299A.
Machine translation of description of Chinese Patent CN101746760A.
Machine translation of description of Chinese Patent CN107540379B.
Machine translation of description of Chinese Patent CN104355290B.
Machine translation of description of Chinese Patent CN101423398A.
Machine translation of description of Chinese Patent CN106011791A.
Machine translation of description of Chinese Patent CN102683722A.
Machine translation of description of Chinese Patent CN101164889B.
Extended European Search Report and Written Opinion from European Application No. EP 17897326.9 dated May 25, 2020.

* cited by examiner

CORE-SHELL CERAMIC PARTICLE COLLOIDAL GEL AND SOLID OXIDE FUEL CELL ELECTROLYTE

RELATED APPLICATIONS

This application claims priority to the Provisional Patent Application No. 62/418,666 filed on 7 Nov. 2016, and Provisional Patent Application No. 62/520,655 filed on 16 Jun. 2017, the teachings of both of which are incorporated herein by reference in their entireties.

GOVERNMENT SUPPORT

This invention was made in part with Government support under contract NSF CMMI 1563537 awarded by the National Science Foundation; and Grant APP-43889 awarded by the State of Colorado Advanced Industries Accelerator Program. The Government has certain rights in the invention.

BACKGROUND

Eight mole percent (8 mol %) yttria-stabilized cubic zirconia ("8YSZ") has practical uses in Solid Oxide Fuel Cells ("SOFCs"), but suffers from some inherent shortcomings such as high operating temperature, high sintering temperature, low ionic conductivity, and poor mechanical strength. The addition of alumina ($Al_2O_3$) by ball milling, a process using high-energy collision of hard balls with a powder mixture of the $Al_2O_3$ and 8YSZ, has been shown to lower the sintering temperature and increase mechanical strength and ionic conductivity.

8YSZ is most commonly used in SOFCs as the solid electrolyte because it is a chemically stable and inexpensive option. The SOFC must be operated at high temperatures, upwards of 700° C., in order to have suitable ionic conductivity. This high operating temperature also limits possible component materials, and requires long start-up times. Further limiting the application of 8YSZ is the high sintering temperature required to make dense SOFC electrolytes. Typically, commercial electrolytes are sintered at 1450° C. for about 4 hours. Because an attractive route to SOFC production is co-firing the electrolyte with all other components, for example, anode, cathode, and interconnect, the material requiring the highest sintering temperature (typically 8YSZ), dictates the co-firing temperature. However, exposure of the non-8YSZ parts to 1450° C. for several hours can have deleterious effects on their performance. There has been an unmet need to minimize both the high sintering temperature and the time requirements.

The expectations for the quality and type of products currently produced by 3D printing with available 3D ink have not been met. 3D printing, including Fused Deposition Modeling (FDM) lays down layers of ink material, with the intent that the layers fuse together, forming a laminated 3-dimensional part. 3D printing, including FDM, lays down layers of ink material, with the intent that the layers fuse together, forming a laminated 3-dimensional part. However, the final parts or output from 3D printing have not been consistently good. The final 3D parts are often fragile, or delaminate easily. The laminate 3D parts may not bond as well in the Z axis as they do in the X-Y planes, so that a force from the side may easily fracture the part.

Further, current 3D part printing is generally not good for production of small parts wherein high resolution is needed. Because the print is in 3 dimensions, resolution depends on the minimum feature size of the X-Y plane, and the Z-axis resolution. Z-axis resolution relates to layer height, and is less related to print quality. The X-Y resolution, or minimum feature size, is measured via microscopic imaging, and is the more important of the two because it allows for production of fine detail in the parts.

BRIEF SUMMARY OF THE DISCLOSURE

The present invention relates, in part, to a discovery of a ceramic particle comprising a core substrate chosen from yttria-stabilized zirconia, partially stabilized zirconia, zirconium oxide, aluminum nitride, silicon nitride, silicon carbide, and cerium oxide; and a conformal coating of a sintering aid film having a thickness of less than three nanometers and covering the core substrate. In one embodiment of the invention, the conformal coating of the sintering aid film covering the core substrate has a thickness of from less than one (1) nanometer to one (1) nanometer. In another embodiment, the conformal coating of the sintering aid film has a thickness of about two (2) nanometers.

In yet another embodiment, the conformal coating of the sintering aid film is a uniform, conformal coating of the core substrate. In another embodiment, the conformal coating of the core substrate includes well-distributed islands of film across the surface of the ceramic particles.

Disclosed herein is a ceramic particle wherein the core comprises yttria-stabilized zirconia or partially stabilized zirconia, and the sintering aid film comprises alumina.

Disclosed herein are methods of forming a ceramic particle comprising a core substrate including a conformal coating of a sintering aid film having a thickness of less than three nanometers, wherein the sintering aid film covering the core substrate is formed by atomic layer deposition ("ALD"). In one embodiment of the invention, the ceramic particle with a conformal coating of a sintering aid film is prepared using one cycle of atomic layer deposition of the sintering aid film; and then sintered in air at about 1350 degrees Celsius for about two (2) hours. In another embodiment of the invention, the ceramic particle is prepared with from about one cycle to about nine cycles of atomic layer deposition of a sintering aid.

Also disclosed herein are methods and compositions relating to a colloidal gel or slurry suitable for producing a 3D ink for 3-dimensional printing comprising a ceramic particle as disclosed herein, including a core substrate and a conformal coating of a sintering aid film having a thickness of less than three nanometers and covering the core substrate.

Another embodiment of the invention is a solid oxide fuel cell electrolyte comprising a ceramic particle as disclosed herein, including a core substrate and a conformal coating of a sintering aid film having a thickness of less than three nanometers and covering the core substrate.

BRIEF DESCRIPTION OF THE DRAWINGS

Embodiments of the invention are further described hereinafter with reference to the accompanying drawings, in which.

DETAILED DESCRIPTION

The invention inter alia also includes the following exemplary embodiments, alone or in combination. It will be understood that the particular embodiments of the invention are shown by way of illustration and not as limitations of the invention. At the outset, the invention is described in its broadest overall aspects, with a more detailed description following.

Disclosed herein are a process comprising adding a thin film of ceramic sintering aid of desired thickness (wt %) to a primary ceramic powder by atomic layer deposition using, for example, an agitated powder reactor, and a product formed by the process. For use in preparing a 3D ink, e.g., incorporation of a conformal coating of the sintering aid around each primary ceramic substrate particle improved the fabricated part properties associated with grain boundary phenomena such as impurity scavenging, grain boundary diffusion, grain growth, liquid-phase sintering, ionic conductivity, thermal conductivity, etc., and increased the homogeneity of dense parts compared with conventional techniques such as ball milling, spray drying, or sol-gel processing. Sintering is the process of causing a material to become a coherent or compact, dense mass by applying heat and/or pressure without melting or liquefying the material. As the terms are used herein, "densification" and "sintering," and grammatical variations thereof, have the same meaning. A sintering aid helps impart integrity and compressive strength to the material being sintered.

Additionally, in the preparation of a ceramic slurry or colloid in, for example, tape casting or additive manufacturing via direct ink writing, the thin film of sintering aid enables facile rheology control by exposing only one surface (the sintering aid), as compared to conventional sintering aid incorporation methods wherein multiple surfaces, and thus multiple surface charges will be present (i.e., the sintering aid and the primary ceramic). For fine ceramic precursor powders that are prone to degradation in aqueous environments, e.g., aluminum nitride (AlN), the thin and pinhole-free conformal coating of an oxide ceramic sintering aid, renders the particles resistant to degradation by water, thereby enabling aqueous processing which is critical in, for example, direct ink writing (additive manufacturing). 3 wt % yttrium oxide is a good sintering agent for aluminum nitride. A more detailed description follows.

Atomic Layer Deposition (ALD), a thin film deposition technique, is a self-limiting surface reaction that deposits uniform layers of the desired precursor onto the particle surface. This is done by fluidizing the particles and adding two different precursors in sequence such that there are two reactions occurring sequentially. For the addition of $Al_2O_3$ to 8YSZ, the reaction utilizes trimethylaluminum (TMA) and water as precursors, adding first TMA, then water, then TMA, and so on. One addition of TMA plus one addition of water comprises one cycle. The reaction proceeds in a fluidized bed reactor to help ensure coating of all surfaces.

Previous studies have investigated the effects of $Al_2O_3$ on the kinetics of 8YSZ densification. In these studies, undoped 8YSZ was compared with samples mixed with $Al_2O_3$ concentrations ranging from 0.1-10 wt % $Al_2O_3$ where $Al_2O_3$ was incorporated using a conventional process such as milling, spray drying, or sol-gel-type processing with the optimal amount for minimizing the sintering temperature and apparent activation energy typically found to be less than (<) 1 wt %.

In accordance with the present invention there is provided a method wherein atomic layer deposition (ALD) was used to add $Al_2O_3$ to 8YSZ as a sintering aid. The effects of the ALD-produced mixture on sintering behavior, kinetics, and ionic conductivity, and for comparison to 8YSZ as purchased were tested. $Al_2O_3$ was deposited as a conformal coating on 8YSZ particles at concentrations ranging from approximately (~) 1 to approximately 4 wt %, corresponding with 1 to 9 ALD cycles, respectively. According to another embodiment of the invention, the mass or weight of the alumina in the sintering aid film is from about 0.2 weight percent to about 2 weight percent of the ceramic particle. For all samples, the addition of $Al_2O_3$ reduced the temperature required for sintering by ~100° C. and decreases the apparent activation energy of densification. The optimal concentration of $Al_2O_3$ was found to be about 2.2 wt % corresponding with about 5 ALD cycles which reduced the apparent activation energy from ~700 kJ/mol to ~400 kJ/mol. A ceramic particle prepared according to an embodiment of the invention is non-reactive with water.

Three Dimensional (3D) Printing Ink

There has been an ongoing need in the 3D ink industry for a method of achieving a more uniform distribution of ceramic and sintering aid, increased reliability and consistency of parts produced, and increased densification with closer packing of particles, which aspects are critical for the production of small parts.

We investigated the effects of the addition of $Al_2O_3$ by ALD on densification and ionic conductivity, developed a strong 3D ink formulation, and successfully printed 3D lattice structures to be further analyzed. With the addition of different amounts of $Al_2O_3$ to 8YSZ, the effects on densification behavior were examined through constant rate of heating experiments using a horizontal push-rod dilatometer. The effects examined included the sintering temperature, the temperature at which the maximum densification rate occurs, the kinetics by which the densification proceeds, the overall ionic conductivity as a function of temperature, and the relative contributions of grain boundary and bulk resistivity. The ink formulation was determined by preparing numerous batches of ink and varying the solids loading and relative polymer amounts in order to obtain the desired rheology for printing with maximum solids vol %. The optimized ink was then used to print 3D structures that were sintered and examined under the SEM.

One embodiment of the invention is a material composition for 3D printing, the composition comprising dispersed solids in a colloid, the solids coated conformally with a solid sintering additive. In another embodiment, the dispersed solids are coated conformally with the solid sintering additive by atomic layer deposition (ALD). In yet another embodiment, the conformal coating is also uniform throughout. The invention inter alia includes the following, alone or in combination.

Prior art ball milling of $Al_2O_3$ and 8YSZ yields only a reasonably uniform distribution of ceramic and sintering aid. However, in contrast to ball milling, using ALD coating of particles yields precise, uniform, conformal coating of 8YSZ ceramic particles with $Al_2O_3$. In coating every substrate particle uniformly by ALD, one can ensure that the sintering aid is utilized throughout the densifying matrix. Uniform, conformal coating also allows use of a lower temperature for densification, which will also reduce the tendency for grain sizes/flaw sizes to grow. The lower temperature also appears to reduce the amount of sintering aid needed to be deposited on the substrate particles in order to achieve high density upon part fabrication.

With prior art methods, it is expected that the incorporation of the sintering aid as a particle additive will result in particulate inclusions at triple grain junctions in the densified matrix. In contrast, when the sintering aid additive is deposited according to an embodiment of our invention as a conformal coating or a uniform, conformal coating by ALD, the additive will exist as an intergranular amorphous thin film, instead of as particulates. The presence of an intergranular, amorphous, uniform, conformal film coating of the ceramic particles enables lower temperature densification and improved homogeneity of dense parts.

Stability is critical for use in 3D printing, or additive manufacturing, and a colloidal gel needs to be prepared from the core/shell substrate/sintering aid particles. Since colloidal properties are the result of fine tuning the dispersion in order to suspend particles in the ink/gel, it is critical to optimize the chemical characteristics of the suspended ceramic particles. For conventional ball-milled precursors, there will be two surfaces (the substrate ceramic and the sintering aid) that require stabilization, and the gel formulation will be a compromise of properties for the substrate and sintering aid. For Particle ALD coatings, there is only one surface to be optimized, that of the sintering aid which surrounds each particle. Hence, it is not only easier to prepare colloidal gels, but also easier to prepare gels that are truly optimized for the system. This improves the preparation of 3D inks/gels having improved flowability for additive manufacturing and ultimately part-to-part reliability.

Importantly, using ALD rather than ball milling, one can use substrate ceramic particles of smaller size, and therefore achieve closer packing and overall improved uniformity of densification. This unexpected result demonstrates the criticality of using ALD to conformally coat substrate ceramic particles in producing 3D ink, and is important for production of very small 3D parts, for which full densification is required.

Solid Oxide Fuel Cells

At least because the ionic resistance of 8YSZ increases with decreasing temperature, the costs of running SOFCs currently remain high because they must be run at high temperatures. Therefore, there is an unmet need of being able to lower the operating temperature of the fuel cell, which can be done by improving the properties of 8YSZ. 8YSZ has a high sintering temperature of 1450° C. However, the addition of $Al_2O_3$ has been demonstrated to lower this temperature, similarly reducing the costs of manufacturing SOFCs. It has also shown positive effects on improving ionic conductivity at lower temperatures which would in turn lower the operating temperature of the SOFC. It may be important that ionic conductivity of 8YSZ remain fairly stable when used in SOFCs.

EXEMPLIFICATION

The primary equipment used for the dilatometer studies included the dilatometer, planetary centrifugal mixer, hydraulic press, and cylindrical steel die. The dilatometer requires ceramic powder compacts that are cylindrical in shape. To achieve this, 8YSZ powder, both with and without $Al_2O_3$, were mixed with a polymeric binder, which was a solution of 2 wt % poly(vinyl alcohol) (Acros Organics, 98.0-98.8% hydrolyzed, average molecular weight ~31,000-50,000 grams/mole) and 98 wt % deionized water. The binder was incorporated by mixing 4 grams of binder, 20 grams of 8YSZ powder, and 25 grams of grinding media (Tosoh Corp., 5 mm diameter, YTZ Grinding Media) in a planetary centrifugal mixer for 30 seconds at 1100 rpm. The planetary centrifugal mixer provides sufficient dispersion of the binder throughout the ceramic powder by simultaneously undergoing high speed revolution and rotation, while the grinding media aids in dispersion.

After sufficient mixing, the 8YSZ powder/binder mixture was separated from the milling media. Cylindrical compacts were made by placing 0.45 grams of 8YSZ powder/binder mixture into a 6 mm inner diameter cylindrical die, which was exposed to 1 ton of pressure for 90 seconds using a hydraulic press. The compact was then ejected from the die and assigned a compact number. Samples were pressed for 8YSZ powder with 0-9 $Al_2O_3$ ALD cycles.

The dilatometer comprises a sample holder, furnace, and push rod to measure displacement. A constant force of 35 centinewton (35 cN) was exerted on the push rod to maintain constant contact with the sample being tested as it shrinks during heating.

Each sample was sintered in air. Before the compact was inserted into the dilatometer, the length was measured and recorded using calipers. The compact number was recorded along with the heating test that was to be run. Constant rate of heating experiments were then carried out as follows: heating rate of 1° C./min from room temperature to 600° C. (binder burnout), desired heating rate (5, 10, 15, or 20° C./min) from 600° C. to 1550° C., cooling back to room temperature at 20° C./min. The linear shrinkage was recorded during these experiments by the dilatometer which was calibrated using a sapphire standard. The shrinkage was then related to density by correcting for the thermal expansion of the samples using the cooling portion of the curves and assuming isotropic shrinkage. As such, these experiments enable the density to be produced as a function of temperature, heating rate, and sample type. The densification rate is then taken as the first derivative of the density with respect to temperature, approximated using finite difference. The density and densification rate can then be used to approximate the apparent activation energy for densification by utilizing an Arrhenius-type dependence of the rate of densification on temperature.

The principal equipment for ink formulation is a high precision scale accurate to 0.1 milligrams and a planetary centrifugal mixer. The centrifugal planetary mixer allows thorough mixing of high viscosity inks. It works by orienting the container at 45° relative to the vertical axis and spinning the container counterclockwise. As the container spins counterclockwise on its own axis, the container is spun along the vertical axis in a clockwise direction which causes vertical spiral convection and exerts a force of 400 G on the ink, effectively evacuating all air as well. The ink formulation begins with a small container fitted for the planetary mixer, which is where the ink will be made and stored. First, YTZ grinding media is added to aid in mixing. 11.56 grams of water was added, then 3.86 grams of ammonium polyacrylate (Darvan 821A) as dispersant. The mass of powder was added in two parts to help ensure uniform mixing. First, 37 grams of 8YSZ powder (coated or uncoated) was added to the aqueous solution which was then placed in the planetary mixer and set to mix for 30 seconds at 1100 rpm. Another 37 grams of 8YSZ powder was added to total 74 grams of powder. It was mixed again for the same time and speed. Next, 1.08 grams of hydroxypropyl methylcellulose (HPMC) were added as a viscosifier to prevent separation of the ink into component parts. The colloidal ink was mixed once more, then the sides were scraped down and it was mixed again. The final ingredient addition is polyethylene imine (PEI) which is in a 40 wt % solution with water to lower viscosity and allow handling. One drop was added, or about 0.02 grams, as a flocculant. The ink was mixed one last time with a final solids volume of 43.5%. The ink was then sealed from air until use.

The principal equipment for direct ink writing and sintering of parts includes a 3D printer, oil bath, and high temperature furnace. So that it may operate with very high precision, the 3D printer utilizes magnets to move. The printer was connected to a computer and operated from there using a specifically designed program. First, a syringe was filled with the prepared 3D ink, and fitted with a tip having a diameter of 330 microns. The oil bath was placed underneath the 3D printer, and the printing substrate was placed in the oil bath. The substrate was a ceramic, and dark in color to allow for visualization of the white ink. To begin printing, the syringe was placed in the printer, and the printer was lowered until just touching the surface of the substrate; then it was raised 200 microns. Rasters, or series of parallel scanning lines, were initiated in order to get the ink flowing smoothly before beginning the print job. Using the computer program, the desired shape was selected and once ready, the printer automatically carried out the print job. Once it completed printing, the piece was removed from the oil bath and left to dry for 48 hours in air. The pieces were sintered in a high temperature tube furnace. The sintering process began with binder burnout, then heated to 1450° C. at a rate of 1.5° C./min; then held at the maximum temperature for 1 hour. It was then cooled at a rate of 20° C./min to room temperature.

The principal equipment for ionic conductivity measurements are a mechanical press, a sintering furnace, and an electrochemical impedance spectrometer. 8YSZ powder (coated or uncoated) were mixed with 2-3 drops poly(vinyl alcohol) and pressed to a thickness of ~0.5" by a mechanical press. Pressed pellets were then densified in air at either 1350° C. or 1450° C. for 2 h. The sintered pellets were then painted with a conductive platinum paste and inserted into a furnace for the electrochemical impedance spectrometry measurements. Ionic conductivity was measured in air at temperatures ranging from 300-800° C.

Figure 1:
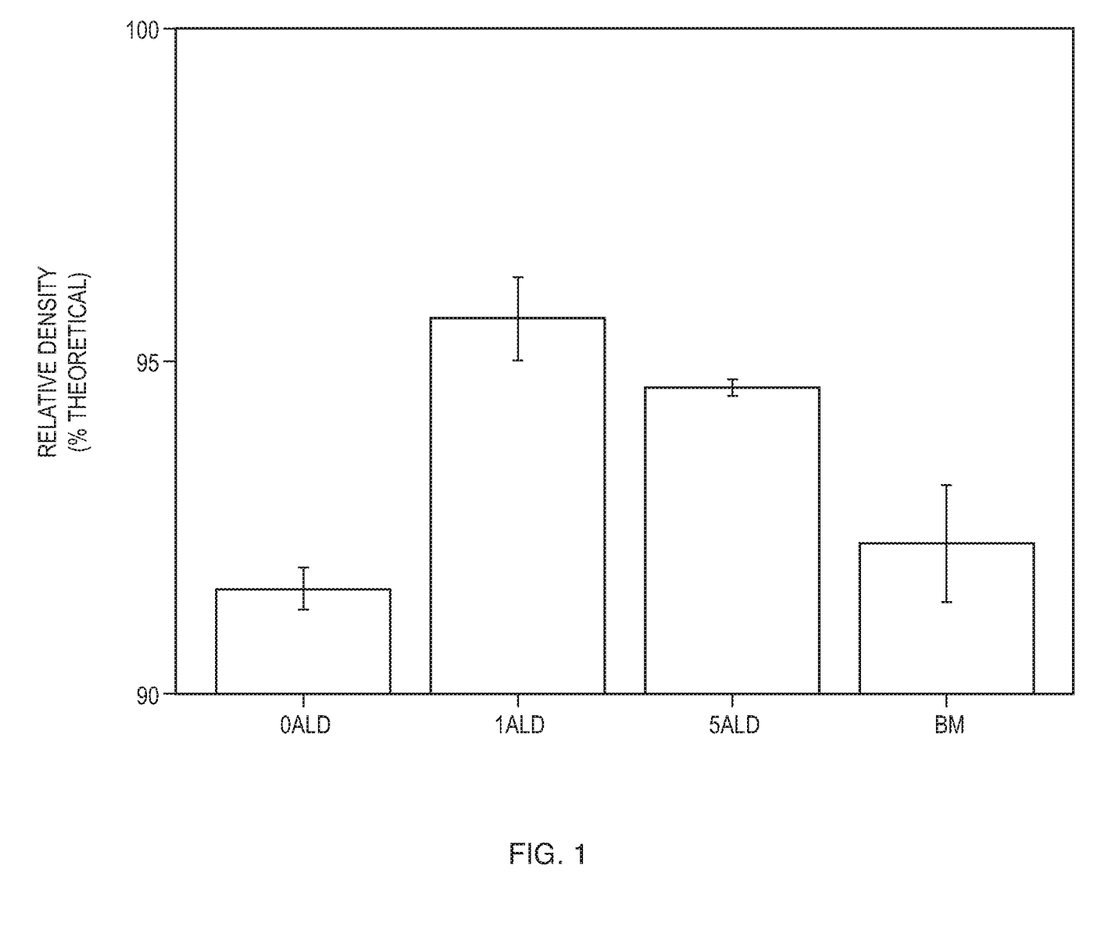
FIG. 1 is a graphical representation of Relative Density measured volumetrically for different sample types having been sintered in air at 1350° C. for 2 hours as a function of the number of ALD cycles, and wherein "BM" represents a Prior Art ball-milled sample.
Figure 2:
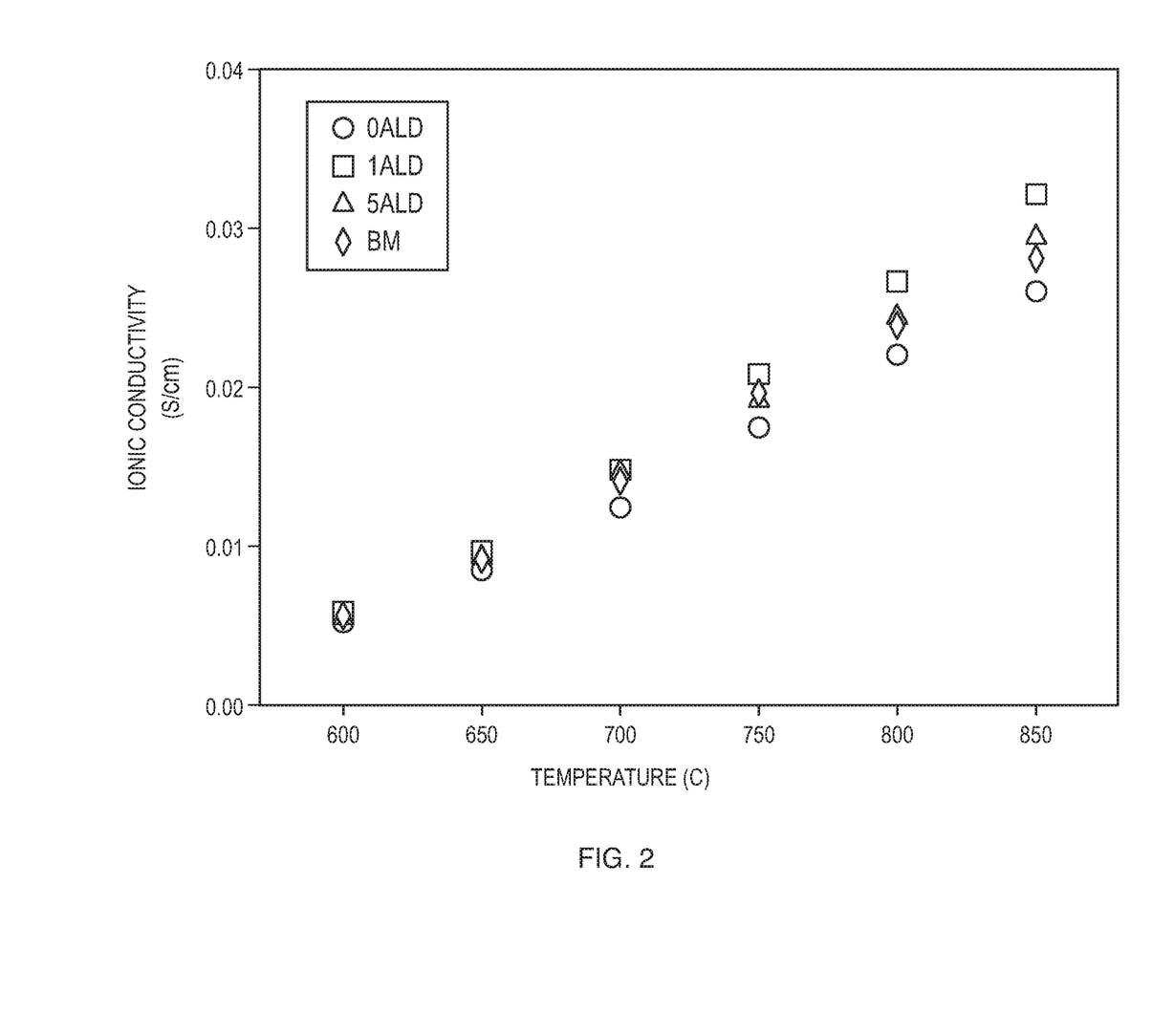
FIG. 2 is a graphical representation of oxygen ion conductivity at different temperatures in ° C., measured using electrochemical impedance spectroscopy for different sample types having been sintered in air at 1350° C. for 2 hours, and wherein "BM" represents a Prior Art ball-milled sample.

Results and Discussion $Al_2O_3$ was deposited on commercial 8YSZ powder by means of ALD. The ALD process exhibited a nearly linear growth rate with number of cycles enabling the deposition of $Al_2O_3$ at a controllable concentration. The $Al_2O_3$ was precisely deposited as a uniform and conformal coating covering each primary 8YSZ particle as a thin amorphous film. The presence of $Al_2O_3$ by ALD enables pellets to reach near theoretical density (>94%) after sintering in air for 2 h at 1350 C. This same density is not reached for either the YSZ with no $Al_2O_3$ or the YSZ with $Al_2O_3$ incorporated by ball milling as seen in FIG. 1.

Figure 3A:
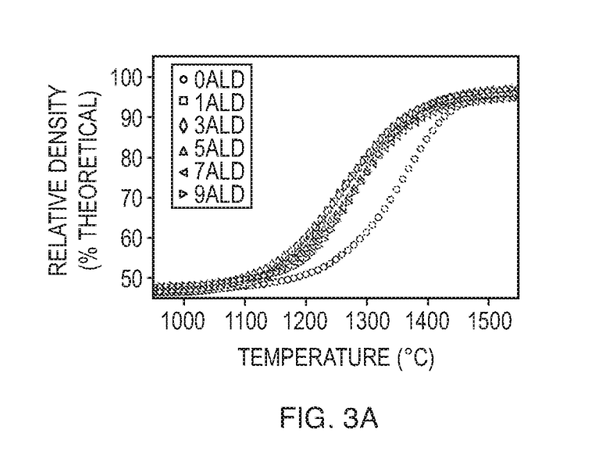
FIG. 3A is a graphical representation of the relative density (% theoretical) as a function of temperature during constant rate of heating at 10° C./min heating rate, in dilatometer experiments for all samples analyzed (coated and uncoated).
Figure 3B:
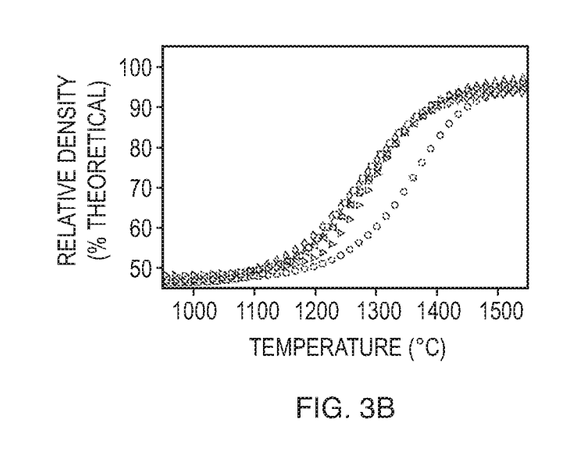
FIG. 3B is a graphical representation of the relative density (% theoretical) as a function of temperature during constant rate of heating at 15° C./min heating rate, in dilatometer experiments for all samples analyzed (coated and uncoated).
Figure 3C:
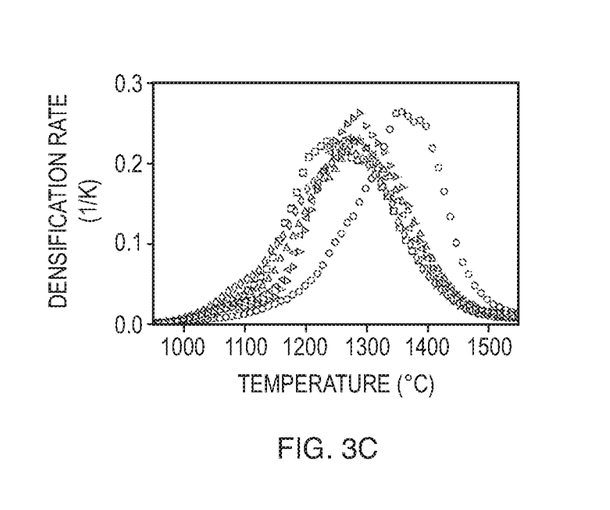
FIG. 3C is a graphical representation of the densification rate (1/K) as a function of temperature during constant rate of heating at 10° C./min heating rate, in dilatometer experiments for all samples analyzed (coated and uncoated).
Figure 3D:
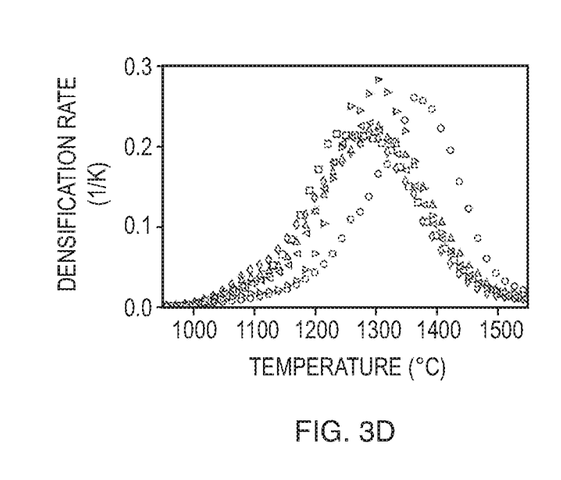
FIG. 3D is a graphical representation of the densification rate (1/K) as a function of temperature during constant rate of heating at 15° C./min heating rate, in dilatometer experiments for all samples analyzed (coated and uncoated).

The precise incorporation of $Al_2O_3$ by ALD decreased the temperature required to sinter/densify by ~100° C. for all $Al_2O_3$ concentrations investigated. FIG. 3A depicts the relative density (% theoretical) as a function of temperature during constant rate of heating at 10° C./min heating rate. FIG. 3B depicts the relative density (% theoretical) as a function of temperature during constant rate of heating at 15° C./min heating rate. For both heating rates, the uncoated samples had less relative density than did the coated samples. Similarly, the densification rate in the initial stage of sintering (relative density <80% theoretical) was found to be greater for all coated samples than the uncoated samples at all temperatures within this regime (FIG. 3C and FIG. 3D.). The temperature at which the maximum densification rate is obtained is similarly decreased by ~100° C. for all coated samples when compared to the uncoated 8YSZ except the 9ALD sample for which the temperature is decreased by <100° C.

Figure 4:
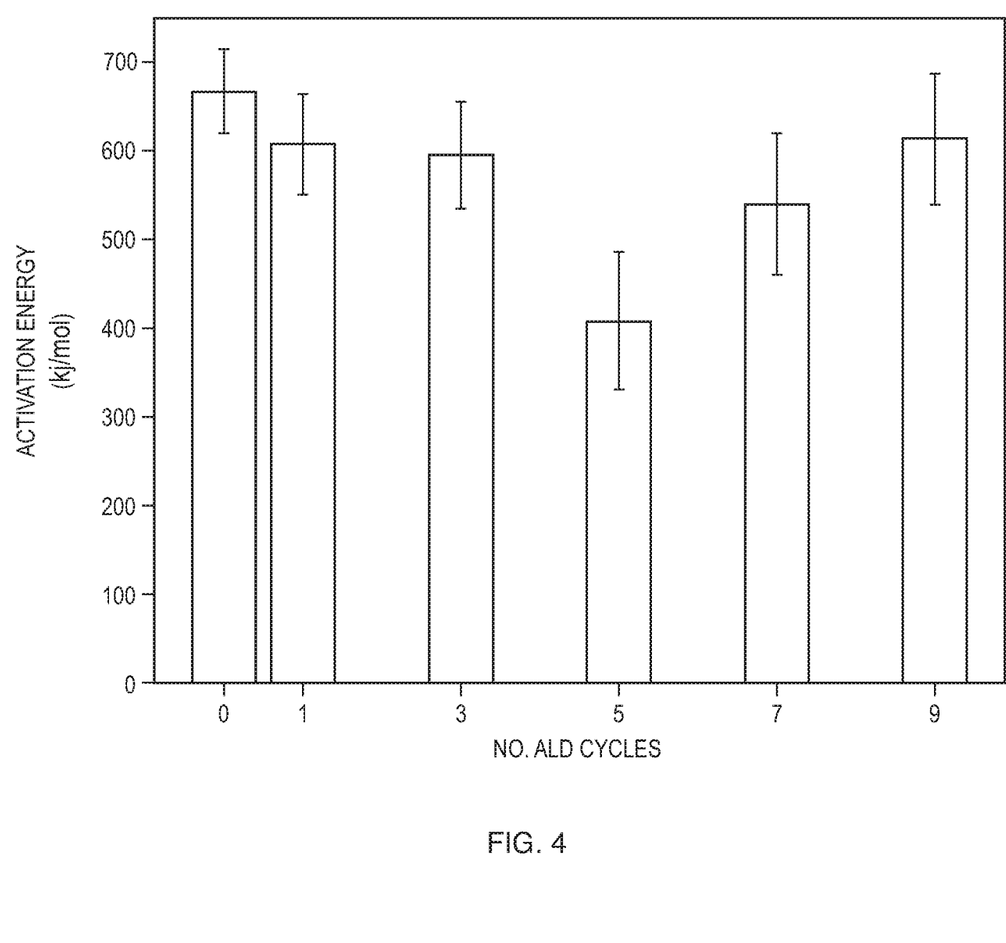
FIG. 4 is a graphical representation of the apparent activation energy of densification as a function of number of ALD cycles, wherein the activation energy was determined from a series of constant rate of heating dilatometer experiments.

An Arrhenius-type analysis of the densification rate as a function of temperature over densities within the initial stage (60-80% density) reveals the apparent activation energy of densification for each sample type. The activation energy is the highest for the uncoated sample, decreases slightly at low $Al_2O_3$ concentrations (1, 3 cycles) and high $Al_2O_3$ concentrations (7, 9 cycles), and decreases significantly at the optimal concentration (of those evaluated) of 5ALD cycles or ~2.2 wt % $Al_2O_3$ (FIG. 4). This dramatic change in activation energy at the 5ALD incorporation level suggests that a conformal ALD film of this thickness (~0.5-0.7 nm) enables a low activation energy diffusion process to occur. It is expected that from about 1 to about 3 ALD cycles, a monolayer does not exist around each 8YSZ particle, instead preferring the formation of small $Al_2O_3$ islands forming a submonolayer of coverage. At 5ALD cycles, we did have a conformal monolayer of $Al_2O_3$ around each substrate particle, ~0.5 nm in thickness. As the number of ALD cycles is increased, this monolayer grows in thickness to ~1-1.4 nm at 9ALD cycles. The minimum activation energy is found for the 5ALD film of ~0.5 nm thickness, suggesting that this is the optimal thickness for an intergranular amorphous film to be thick enough to dissolve sufficient cations ($Zr^{4+}$) but thin enough to enable facile diffusion from grain to grain. At lower thicknesses, the intergranular diffusion path will be insufficiently formed. At higher thicknesses, the film will be sufficiently thick to act in part as a barrier to intergranular diffusion.

Figure 5:
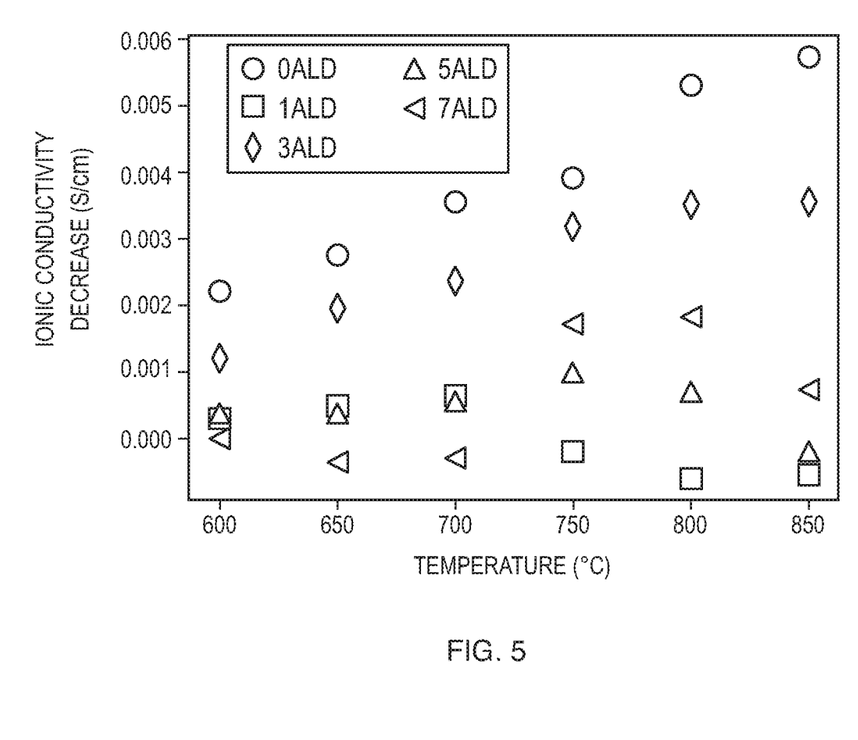
FIG. 5 is a graphical representation of the decrease in ionic conductivity (S/cm) when decreasing the sintering temperature from 1450° C. to 1350° C. as a function of measurement temperature and number of ALD cycles, wherein conductivity was measured using electrochemical impedance spectroscopy.

A reduction in sintering temperature is expected to have deleterious effects on the ionic conductivity of 8YSZ electrolytes due in part to the retention of pores or defects in the microstructure. Ionic conductivity measurements were obtained for 8YSZ (coated and uncoated) using electrochemical impedance spectrometry following two sintering procedures—1450° C. for 2 h and 1350° C. for 2 h. The decrease in conductivity accompanying the decrease in sintering temperature was found to be diminished for all coated samples evaluated (1-7 ALD cycles). The conductivity decrease is similarly expected to be measurement temperature-dependent. However, we found the ionic conductivity decrease to be approximately constant as a function of impedance temperature, with the exception of the 3ALD sample. As such, the $Al_2O_3$ ALD coatings demonstrate that a reduction in sintering temperature is not accompanied by a reduction in ionic conductivity (electrolyte performance) as is the case in the uncoated sample. The ionic conductivity of samples sintered at 1350 C for 2 h was found to be optimized or maximized with 1 ALD cycle of $Al_2O_3$ (0.7 wt %) as seen in FIG. 5. The performance of this sample was found to be superior to YSZ with no $Al_2O_3$ and YSZ with $Al_2O_3$ incorporated by ball milling. Ionic conductivity decrease is defined as (conductivity after sintering at 1450 C minus conductivity after sintering at 1350 C). Coated samples outperformed the uncoated sample at all temperatures. The benefit of the ALD coatings increases with temperature.

Figure 6:
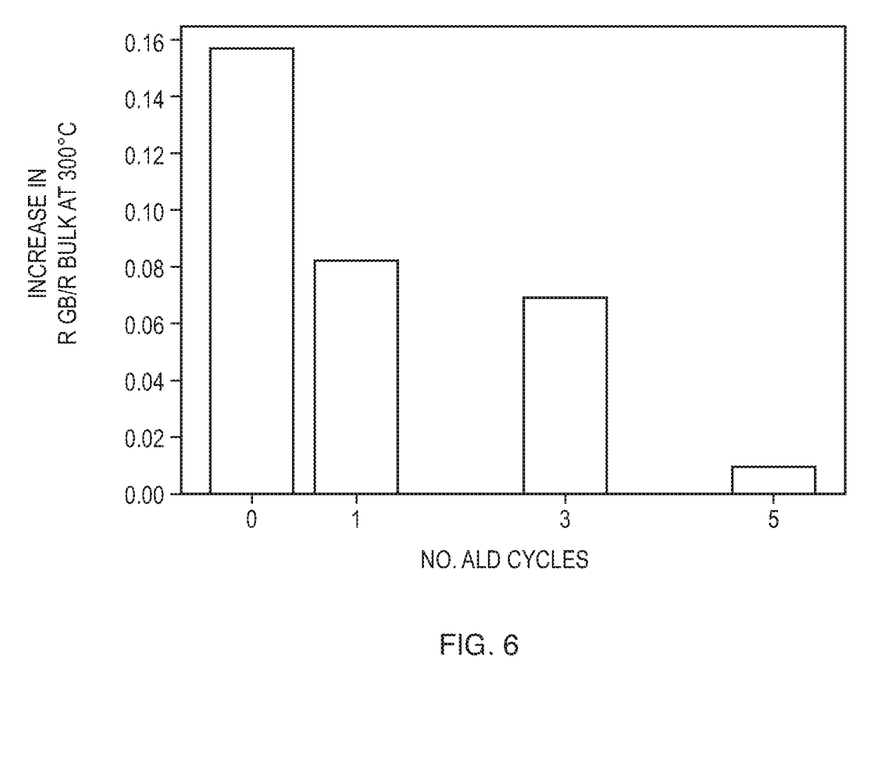
FIG. 6 is a bar graph showing, for zero to 5 ALD cycles, the increase in R GB/R bulk at 300° C. defined as (the ratio of grain boundary resistivity to bulk resistivity after sintering at 1450° C. for 2 h) minus (the ratio of grain boundary resistivity to bulk resistivity after sintering at 1350° C. for 2 h) as measured using electrochemical impedance spectroscopy at 300° C. in air.

Low temperature (300° C.) electrochemical impedance spectrometry can be used to decouple the relative contributions of the grain boundaries and the grain interior to the total resistivity of the electrolyte. Following sintering at two temperatures as described previously, we note the increase in grain boundary resistivity is significant for the uncoated sample but less so for the coated samples, particularly for the 5ALD sample (FIG. 6). This suggests that the ALD coatings sufficiently alter the microstructure, and particularly the grain boundary microstructure, such that resistivity at the grain boundary is reduced following reduced temperature sintering compared with the uncoated sample.

Colloidal gel ink formulations were developed for 8YSZ with 0, 1, and 3 $Al_2O_3$ ALD cycles. For 8YSZ with 0 $Al_2O_3$ ALD cycles, the optimum solids volume percentage was found to be between 43.5 vol % to just under 44 vol %. A printable 8YSZ ink can be made with 44 vol % solids, but it is prone to thickening with time, causing the printer to clog and stall, rendering the printed part unusable. However, inks consisting of 43.5 vol % solids could be printed reliably, and had a high viscosity to resist deformation and retain their shape after extrusion. Additionally, it was shown that the ink formation with 43.5 vol % solids content experiences minimal warping and uniform shrinkage after densification. At a solids loading greater than 44 vol %, the colloidal ink collapses and becomes unprintable and firm. The polyelectrolyte, Darvan, no longer effectively disperses the mixture and phases of liquid and powder begin to separate. Solids loading less than 43 vol % leads to deformation after extrusion, and an increased likelihood of warping and cracking during drying and densification. The final optimized ink formulation for 8YSZ with 0 $Al_2O_3$ cycles was 43.5 vol % 8YSZ powder, 41.5 vol % water, 11.1 vol % Darvan, 3.8 vol % hydroxypropyl methylcellulose, and 0.2 vol % PEI.

The optimized ink formulation for 8YSZ was then extended to 8YSZ with 1 and 3 $Al_2O_3$ ALD cycles. The ink formulation for 8YSZ with 1 $Al_2O_3$ ALD cycle was 42.4 vol % 8YSZ/$Al_2O_3$ powder, 42.0 vol % water, 11.4 vol % Darvan, 4.1 vol % hydroxypropyl methylcellulose, and 0.2 vol % PEI. Additionally, the ink formulation for 8YSZ with 3 $Al_2O_3$ ALD cycles was 39.4 vol % 8YSZ/$Al_2O_3$ powder, 44.8 vol % water, 12.2 vol % Darvan, 3.4 vol % hydroxypropyl methylcellulose, and 0.2 vol % PEI. Both these formulas led to the successful fabrication of 3D square lattice structures using direct ink writing, where clogging did not occur during printing and final parts did not warp or deform.

The rheology of the ink chosen is highly dependent on the surface chemistry of the ceramic particles. A solution of 8YSZ and water has a pH of approximately 7 and, with a basic isolectric point, the 8YSZ surface becomes positively charged. Van der Waals forces cause the 8YSZ particles to agglomerate, so the a negatively changed polyelectrolyte, Darvan, was added to homogeneously disperse the 8YSZ powder through electrosteric repulsion. The dispersant allows for ink homogeneity, but a flocculant must be added to ensure the ink is stronger and has desirable mechanical properties to resist deformation. The flocculant added was PEI, which is a positively charged polyelectrolyte. A small amount was added so that some, but not all, of the dispersant effects were countered. Viscosity was adjusted by adding hydroxypropyl methylcellulose, and ensured that the ink would not separate out into individual components. The final result was a homogenous, viscous ink that prints without separating and holds it shape during extrusion, drying, and densification.

It was found that the ink formulations for 8YSZ with 0, 1, and 3 $Al_2O_3$ ALD cycles required similar amount of dispersant and flocculant, only varying slightly in water and Darvan content, to control the particle surface chemistry and produce an ink with required rheology. The ink formulation is dependent on the particle surface chemistry, and at 1 and 3 $Al_2O_3$ ALD cycles, only a sub-monolayer of $Al_2O_3$ is present. The particle surface consists of both 8YSZ and $Al_2O_3$. Therefore, it can be seen that the particle surface chemistry of both 8YSZ and 8YSZ with 1 and 3 $Al_2O_3$ cycles respond similarly to the polyelectrolytes utilized in the production of the colloidal gel ink.

It was also found that a significant amount of shrinkage occurs during densification for 3D printed colloidal gel inks. For 8YSZ with 0 $Al_2O_3$ ALD cycles, the initial dimensions of all printed parts are approximately 35.3 mm by 35.5 mm. After drying the dimensions are 34.7 mm by 34.8 mm, which is a shrinkage of about 4%. The dimensions of the sintered pieces on average are 27.3 mm by 26.9 mm, which is a shrinkage of about 40%. This is due to the elimination of water, hydroxypropyl methylcellulose, Darvan, and PEI from the part and the reduction of pores from between ceramic grains.

According to an embodiment of the invention, a ceramic particle has a conformal coating of the sintering aid film covering the core substrate, and is formed by atomic layer deposition using a system chosen from a fluid bed reactor, a vibrating reactor, a rotating reactor, a spatial system wherein precursor gases are separated in space, and a batch reactor, and any desired combinations thereof.

A ceramic particle according to an embodiment of the invention has a core comprising cerium oxide and a sintering aid film chosen from alumina, titanium oxide, yttrium oxide, calcium oxide, iron oxide, copper oxide, chromium oxide, boron oxide, silicon dioxide, nickel oxide, and any desired combinations thereof. In another embodiment, the core of the ceramic particle comprises aluminum nitride, and the sintering aid film is chosen from yttrium oxide, magnesium oxide, calcium oxide, silicon dioxide, lanthanum oxide, and any desired combinations thereof.

A ceramic particle according to an embodiment of the invention has a core chosen from silicon nitride and silicon carbide, and the sintering aid film is chosen from yttrium oxide, alumina, magnesium oxide, lutetium oxide, ytterbium oxide, and any desired combinations thereof.

Analysis and Recommendations

The precise coating of 8YSZ with $Al_2O_3$ by ALD is effective in reducing the sintering temperature and temperature at which the maximum rate of densification is obtained by ~100° C. The apparent activation energy for densification was found to similarly decrease for all coated samples when compared with the uncoated 8YSZ. The optimal level of ALD incorporation for maximally reducing the apparent activation energy was found to be 5 ALD cycles or ~2.2 wt % $Al_2O_3$.

The precise conformal coating of 8YSZ with $Al_2O_3$ by ALD is similarly effective in enabling sufficiently conductive electrolytes when utilizing a reduced sintering temperature. For this application, 1 ALD cycle or ~0.7 wt % $Al_2O_3$ was found to be the optimal, although 5 and 7 ALD cycles (~2.2 and ~3.3 wt %) perform similarly. At low temperature (300° C.), the resistivity of the grain boundaries is decreased substantially after sintering at low temperature for the coated samples, particularly the sample with 5 ALD cycles.

For uncoated 8YSZ powder, a colloidal gel ink formulation with maximum solids loading was determined to reliably produce 8YSZ ceramic parts that did not warp or deform during sintering. The colloidal gel ink formulation for 8YSZ powder was then modified for 8YSZ powder with an $Al_2O_3$ coating by 1 and 3 $Al_2O_3$ ALD cycles, and the formulation was determined to reliably print ceramic parts from core/shell 8YSZ/$Al_2O_3$ powder that did not warp or deform during sintering. The addition of an $Al_2O_3$ coating to 8YSZ powder reduces the sintering temperature in comparison to uncoated 8YSZ powder. That is, one can print and sinter/densify uncoated 8YSZ powder, but it would require higher densification temperatures to do so than is required for parts produced from 8YSZ powder with a coating from 1 and 3 $Al_2O_3$. ALD cycles.

3YSZ represents zirconia doped with three mole percent (3 mol %) yttria. 3YSZ is also referred to as "Y-TZP." The colloidal gel ink formulation for 3YSZ (partially stabilized zirconia or Y-TZP), conformally coated with alumina by atomic layer deposition, was adjusted and optimized. ALD coating of zirconium ceramic particles with alumina should be beneficial as a sintering aid for any level of yttrium doping of zirconium oxide. In practice, we found that the amount of doping can be varied slightly from about 3 percent to about 8 percent in order to obtain different properties.

The dopant concentration in zirconia dictates the crystal structure of the material. Zirconia doped with three mole percent, 3YSZ, is the mechanically strong tetragonal phase, and has been used in dental ceramics. We herein disclose that when 20 wt % $Al_2O_3$ is added by ALD as a conformal coating to 3YSZ (ATZ) the mechanical properties are further enhanced. Alumina toughened zirconia (ATZ) ceramics, wherein the alumina has been added as a conformal coating by ALD, could be important materials for use in biomedical implants and other engineering applications requiring high strength and abrasion resistance at ambient temperature.

As the terms are used herein, the number preceding the "YSZ" indicates the molar percentage doping by yttria. 8 mol % doping optimally stabilizes the cubic crystal structure of $ZrO_2$ which is preferred for oxygen ion conduction (e.g., in a solid electrochemical device). 8YSZ is commonly referred to as "yttria-stabilized zirconia," "yttria-stabilized cubic zirconia," "cubic stabilized zirconia," or "fully stabilized zirconia." 3YSZ can also be referred to as "yttria-stabilized zirconia," but is more commonly referred to "tetragonal zirconia polycrystal," "TZP," "Y-TZP," "tetragonal polycrystalline zirconia", "yttria-stabilized tetragonal zirconia", or "partially stabilized zirconia."

Other "stabilizers" such as $Sc_2O_3$ can also be used to control the crystal structure of $ZrO_2$ in the same manner as $Y_2O_3$. In yet other embodiments of the invention, the $Al_2O_3$ sintering aid deposited by atomic layer deposition should be beneficial also in these cases.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including the accompanying drawings), and/or all of the steps of any method or process so disclosed, may be combined in any combination, except combinations where at least some of such features and/or steps are mutually exclusive. The drawings in the Figures are not necessarily to scale. The invention is not restricted to the details of any foregoing embodiments. The invention extends to any novel one, or any novel combination, of the features disclosed in this specification (including any accompanying drawings), or to any novel one, or any novel combination, of the steps of any method or process so disclosed.

EQUIVALENTS

While this invention has been particularly shown and described with references to preferred embodiments thereof, it will be understood by those skilled in the art that various changes in form and details may be made therein without departing from the scope of the invention.

What is claimed is:

1. A colloidal gel comprising:
   ceramic particles comprising a core substrate chosen from yttria-stabilized zirconia, partially stabilized zirconia and cerium oxide, and a coating of a sintering aid film comprising alumina and having a thickness of less than three nanometers and covering the core substrate and wherein the coating is prepared with 1 to 9 cycles of atomic layer deposition;
   water;
   a dispersant;
   a viscosity adjusting agent; and
   a flocculant.

2. The colloidal gel of claim 1, wherein the coating of the sintering aid film covering the core substrate has a thickness of from less than one nanometer to one nanometer.

3. A solid oxide fuel cell electrolyte made by sintering the particles of claim 1.

4. The colloidal gel of claim 1, wherein the atomic layer deposition uses a system chosen from a fluid bed reactor, a vibrating reactor, a rotating reactor, a spatial system wherein precursor gases are separated in space, and a batch reactor, and any combinations thereof.

5. The colloidal gel of claim 1, wherein the core substrate is yttria-stabilized zirconia and the sintering aid film coating comprises approximately 2.2 wt % alumina added by atomic layer deposition wherein wt % refers to wt % of the ceramic particle.

6. The colloidal gel of claim 1, wherein the core substrate is partially stabilized zirconia.

7. The colloidal gel of claim 1, wherein the core substrate is cerium oxide.

8. The colloidal gel of claim 1, wherein the ceramic particles are prepared with one cycle of atomic layer deposition and wherein the coating of a sintering aid film has a thickness of less than one monolayer.

9. The solid oxide fuel cell electrolyte of claim 3, having a higher ionic conductivity in the temperature range of 750° C. to 850° C. as compared with particles of the same composition but with a thicker coating.

10. The colloidal gel of claim 1, wherein the core substrate is yttria-stabilized zirconia, and a yttrium oxide doping of the yttria-stabilized zirconia is about 8 mol %.

11. The colloidal gel of claim 1, wherein the core substrate is partially stabilized zirconia and a yttrium oxide doping of the partially stabilized zirconia is about 3 mol %.

12. The colloidal gel of claim 1, wherein the core substrate is partially stabilized zirconia and a yttrium oxide doping of the partially stabilized zirconia is about 4 mol %.

13. The colloidal gel of claim 1, wherein the mass or weight of the alumina in the sintering aid film is from about 0.2 wt % to about 2 wt % of the ceramic particle.

14. The colloidal gel of claim 1, wherein the coating of the sintering aid film covering the core substrate comprises islands of film across the surface of the ceramic particle.

15. The solid oxide fuel cell electrolyte of claim 3 wherein the coating of the sintering aid film is prepared with one cycle of atomic layer deposition and sintered in air at about 1350° C. for about 2 hours.

16. The solid oxide fuel cell electrolyte of claim 3, wherein the ceramic particles are prepared with from one cycle to 7 cycles of atomic layer deposition.

17. The solid oxide fuel cell electrolyte of claim 3, wherein the ceramic particle is prepared with 5 cycles of atomic layer deposition.

18. A colloidal gel ink comprising the ceramic particle of claim 1, wherein the core substrate is yttria-stabilized zirconia or 8YSZ, and wherein the colloidal gel ink comprises 42.4 volume % to 44.8 volume percent solids, and wherein a thickness of the alumina coating is less than one monolayer.

19. A solid oxide fuel cell electrolyte comprising the ceramic particle of claim 1, wherein the ceramic particles are sintered.

20. The colloidal gel of claim 1, wherein the dispersant comprises ammonium polyacrylate.

21. The colloidal gel ink of claim 18, wherein the core substrate comprises 8YSZ.

22. The colloidal gel or slurry of claim 1, wherein the coating of the sintering aid film is a uniform, conformal coating of the core substrate.

23. An electrolyte comprising sintered ceramic particles, each ceramic particle comprising:
a core substrate comprising yttria-stabilized zirconia; and
a coating of a sintering aid film having a thickness of from less than one (1) nanometer to one (1) nanometer.

24. The colloidal gel of claim 8, wherein the flocculant comprises polyethylene imine.

25. The colloidal gel or slurry of claim 24, wherein the viscosity adjusting agent comprises hydroxypropyl methylcellulose.

* * * * *